US009474766B2

(12) United States Patent
Marriage et al.

(10) Patent No.: US 9,474,766 B2
(45) Date of Patent: Oct. 25, 2016

(54) USE OF A REDUCED CALORIE INFANT FORMULA CONTAINING NUCLEOTIDES AND/OR CAROTENOIDS FOR REDUCING ADVERSE HEALTH EFFECTS LATER IN LIFE

(71) Applicant: ABBOTT LABORATORIES, Abbott Park, IL (US)

(72) Inventors: Barbara J. Marriage, Columbus, OH (US); Christine L. Gallardo, New Albany, OH (US); Christina Sherry, Westerville, OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 14/367,518

(22) PCT Filed: Dec. 4, 2012

(86) PCT No.: PCT/US2012/067712
§ 371 (c)(1),
(2) Date: Jun. 20, 2014

(87) PCT Pub. No.: WO2013/180747
PCT Pub. Date: Dec. 5, 2013

(65) Prior Publication Data
US 2015/0011498 A1    Jan. 8, 2015

Related U.S. Application Data

(60) Provisional application No. 61/580,442, filed on Dec. 27, 2011.

(51) Int. Cl.
*A01N 43/04* (2006.01)
*A61K 31/70* (2006.01)
*A61K 31/708* (2006.01)
*A23L 1/29* (2006.01)
*A23L 1/30* (2006.01)
*A23L 1/303* (2006.01)
*A23L 1/275* (2006.01)
*A61K 31/01* (2006.01)
*A61K 31/015* (2006.01)
*A61K 31/047* (2006.01)
*A61K 31/7068* (2006.01)
*A61K 31/7076* (2006.01)

(52) U.S. Cl.
CPC ............ *A61K 31/708* (2013.01); *A23L 1/2753* (2013.01); *A23L 1/296* (2013.01); *A23L 1/303* (2013.01); *A23L 1/3012* (2013.01); *A61K 31/01* (2013.01); *A61K 31/015* (2013.01); *A61K 31/047* (2013.01); *A61K 31/7068* (2013.01); *A61K 31/7076* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| 7,090,879 | B2 * | 8/2006  | Albrecht et al. ............ 426/72 |
| 8,076,282 | B2   | 12/2011 | Hageman |
| 2008/0269330 | A1 | 10/2008 | Stahl et al. |
| 2009/0118227 | A1 | 5/2009  | Jouni et al. |
| 2009/0274662 | A1 | 11/2009 | Magowan et al. |
| 2010/0092610 | A1 | 4/2010  | Haschke et al. |
| 2011/0034407 | A1 | 2/2011  | Nieuwenhuizen et al. |
| 2011/0129573 | A1 | 6/2011  | Albrecht et al. |

FOREIGN PATENT DOCUMENTS

| CN | 101951794   | 1/2011 |
| EP | 1932437     | 6/2008 |
| EP | 2283736     | 2/2011 |
| JP | 2003-95930  | 4/2003 |
| TW | 200845917   | 12/2008 |
| TW | 201121431   | 7/2011 |
| WO | 2007/050521 | 5/2007 |
| WO | 2008/071667 | 6/2008 |
| WO | 2010112429  | 10/2010 |
| WO | 2013180747  | 12/2013 |

OTHER PUBLICATIONS

International Search Report for PCT/US2012/067712 dated Jan. 20, 2014.
International Preliminary Report on Patentability for PCT/US2012/067712 dated Jul. 1, 2014.
English translation of Office Action and Search Report in TW 101145555 dated Apr. 23, 2014.
Litonjua, Augusto, et al., "Asthma and obesity: Common early-life influences in the inception of disease," J. of Allergy and Clinical Immunology, vol. 121, No. 5, pp. 1075-1084, May 1, 2008.
Demmelmair, et al., "Long-term consequences of early nutrition," Early Human Development, Shannon, IR, vol. 82, No. 8, pp. 567-574, Aug. 1, 2006.
Galic, et al., "Hematopoietic AMPK beta 1 reduces mouse adipose tissue macrophage inflammation and insulin resistance in obesity," J. of Clinical Investigation, vol. 121, No. 12, pp. 4903-4915 Dec. 1, 2011.
Suzuki, et al., "Relationship between obesity and serum markers of oxidative stress and inflammation in Japanese," Asian Pacific Journal of Cancer Prevention, Asian Pacific Organization for Cancer Prevention, vol. 4, No. 3, pp. 259-266 Jul. 1, 2003.
Rule 161 and 162 Communication for EP Application No. 12871602.4 dated Aug. 5, 2014.
First Office Action in VN 1-2014-02509 dated Nov. 24, 2014.
Office Action for CA Application No. 2,861,547 dated May 11, 2015.

(Continued)

*Primary Examiner* — Patrick Lewis
(74) *Attorney, Agent, or Firm* — Calfee, Halter & Griswold LLP

(57) ABSTRACT

The present disclosure is directed to reduced calorie infant formulas, and in particular, reduced calorie infant formulas that have at least one nucleotide and/or at least one carotenoid for reducing inflammation-related diseases later in life. Particularly, the reduced calorie infant formulas reduce the risk of obesity later in life.

16 Claims, 3 Drawing Sheets

(56) References Cited

OTHER PUBLICATIONS

First Examination Report in NZ 626,947 dated Mar. 18, 2015.
Office Action for CA Application No. 2,861,547 dated Feb. 16, 2016.
First Office Action for CN 201280070672.9 dated May 29, 2015.
Second Office Action for CN 201280070672.9 dated Jan. 5, 2016.
Further Examination Report Postponed Acceptance for NZ 626,947 dated Dec. 17, 2015.
Search Report and Written Opinion for SG 11201403712X dated Jul. 3, 2015.
Written Opinion for SG 11201403712X dated Feb. 15, 2016.
Ford, E.S. et al., "Serum Carotenoid Concentrations in US Children and Adolescents," Am. J. Clin. Nutr., Oct. 2002, vol. 76, No. 4, pp. 818-827.
Gunther, et al., "Early Protein Intake and Lated Obesity Risk: Which Protein Sources at Which Time Points Throughout Infancy and Childhood are Important for Body Mass Index and Body Fat Percentage at 7 Years of Age?", Am. J. Clin. Nut., Dec. 2007, vol. 86, No. 6, pp. 1765-1772.
Koletzko, et al., "Lower Protein in Infant Formula is Associated with Lower Weight Up to Age 2 Years: A Randomized Clinical Trial," Am. J. Clin. Nutr., Apr. 22, 2009, vol. 89, No. 6, pp. 1836-1845.
Riva, et al., "Closer to the Gold Standard: An Appraisal of Formulae Available in Italy for Use in Formula-Fed Infants," J. Int. Med. Res., Nov. 2005, vol. 33, No. 6, pp. 595-611.
Sami et al., "Serum Retinol and Total Carotene Concentrations in Obese Pre-School Children," Med. Scit. Monit., Nov. 1, 2005, vol. 11, No. 11, pp. CR510-CR514.

* cited by examiner

USE OF A REDUCED CALORIE INFANT FORMULA CONTAINING NUCLEOTIDES AND/OR CAROTENOIDS FOR REDUCING ADVERSE HEALTH EFFECTS LATER IN LIFE

CROSS REFERENCE TO RELATED APPLICATIONS

This application is the U.S. national stage entry of PCT/US2012/067712 with an international filing date of Dec. 4, 2012, which is herein incorporated by reference in its entirety and which claims priority to and any other benefit of U.S. Provisional Patent Application No. 61/580,442, filed Dec. 27, 2011, the disclosure of which is herein incorporated in its entirety by reference.

FIELD OF THE DISCLOSURE

The present disclosure is directed to the use of reduced calorie infant formulas including nucleotides and/or carotenoids for reducing long term adverse health effects, including obesity, later in life. Also disclosed are reduced calorie, reduced protein infant formulas including nucleotides and/or carotenoids for reducing long term adverse health effects, including obesity, later in life.

BACKGROUND OF THE DISCLOSURE

The inflammatory response is an attempt by the body to restore and maintain homeostasis after invasion by an infectious agent, antigen challenge, or physical, chemical or traumatic damage. While the inflammatory response is generally considered a healthy response to injury, the immune system can present an undesirable physiological response if it is not appropriately regulated. Specifically, unregulated oxidation and associated inflammation are major causes of tissue damage and clinically significant disease in preterm and term infants. This is due in large part to the immaturity in function of the natural immune system of infants, and especially preterm infants.

Inflammation is one of the leading mechanisms of non-communicable diseases in the world, in particular, obesity and its co-morbidities. For example, obesity is characterized by chronic low-grade inflammation in adipose tissue which contributes to insulin resistance, type 2 diabetes (non-insulin dependent diabetes mellitus), and cardiovascular disease. Cytokine secreted by cells of the innate immune system (i.e., macrophages) and adipose tissues (e.g., adipokines) are believed to be the key to regulating the inflammatory milieu. In particular, IL-1β, TNF-α, and activation of the NF-κB pathway have been linked to the negative metabolic effects of obesity, including cardiovascular disease and type 2 diabetes. Furthermore, inhibition of several independent arms of the NF-κB pathway shows less weight gain, increased insulin sensitivity, improved lipid profile, and decreased inflammation.

Breastfeeding has been associated with enhanced development and balanced growth and maturation of the infant's immune systems, thereby providing protection of the infant to infection and inflammatory-related diseases. Breast milk appears to contain antioxidants, such as superoxide dismutase, glutathione peroxidase and catalase, or other non-enzymatic antioxidants such as glutathione, lactoferrin and polyphenols, in addition to antioxidants, such as vitamins A, C, E and selenium.

Not all infants receive human breast milk. Further, no vaccines are currently available for the prevention of inflammatory-related diseases, such as obesity and insulin resistance. Therefore, development of safe and efficacious preventative or therapeutic methods would be beneficial, especially for infants. Particularly, infant formulas designed to be closer to breast milk in terms of composition and function would provide a benefit to these infants.

It would therefore be desirable to provide an infant formula that could mimic the antioxidative protective effects of breast milk. It would be further advantageous if the formulas could reduce the risk of inflammatory-related diseases, such as obesity, later in life.

SUMMARY OF THE DISCLOSURE

The present disclosure is directed to the use of nutritional formulas, and specifically reduced calorie or reduced calorie/reduced protein infant formulas, including at least one nucleotide and/or at least one carotenoid for reducing the risk of some potentially inflammatory-related diseases later in life, and particularly obesity later in life. The nucleotide and/or carotenoid included in the reduced calorie infant formulas may modulate immune responses to inflammatory stimuli, thereby reducing inflammation and its adverse health effects. The reduced calorie formulas of the present disclosure, when administered to infants during the first year of life, further provide adequate nutrition for the growth and development of the infant.

Thus, in one embodiment, the present disclosure is directed to a method of reducing obesity later in life. The method comprises administering to an infant in need thereof an infant formula in the first year of life, wherein the infant formula has an energy content of less than 650 Kcal/L and comprises at least one nucleotide.

In another embodiment, the present disclosure is directed to a method of reducing obesity later in life. The method comprises administering to an infant in need thereof an infant formula in the first year of life, wherein the infant formula has an energy content of less than 650 Kcal/L and comprises at least one carotenoid.

In another embodiment, the present disclosure is directed to a method of reducing obesity later in life. The method comprises administering to an infant in need thereof an infant formula in the first year of life, wherein the infant formula has an energy content of less than 650 Kcal/L and comprises at least one nucleotide and at least one carotenoid.

In another embodiment, the present disclosure is directed to an infant formula comprising an energy content of less than 650 Kcal/L and comprising at least one nucleotide, for reducing the risk of obesity later in life.

In another embodiment, the present disclosure is directed to an infant formula comprising an energy content of less than 650 Kcal/L and comprising at least one carotenoid, for reducing the risk of obesity later in life.

In another embodiment, the present disclosure is directed to an infant formula comprising an energy content of less than 650 Kcal/L and comprising at least one nucleotide and at least one carotenoid, for reducing the risk of obesity later in life.

It has now surprisingly been discovered that reduced calorie infant formulas that include a nucleotide alone, a carotenoid alone, or a combination of a nucleotide and a carotenoid, in sufficient amounts may reduce inflammatory-related diseases later in life, and in particular obesity later in life.

It has also been discovered that the reduced calorie infant formulas that include a nucleotide alone, a carotenoid alone, or a combination of a nucleotide and a carotenoid, can reduce the risk of insulin resistance, type 2 diabetes (non-insulin dependent diabetes mellitus), cardiovascular disease, and atherosclerosis later in life. Particularly, through anti-inflammatory strategies, chronic inflammation that can damage tissue is minimized, preventing and/or delaying the development of these diseases later in an infant's life.

DETAILED DESCRIPTION OF THE DISCLOSURE

Figure 1:
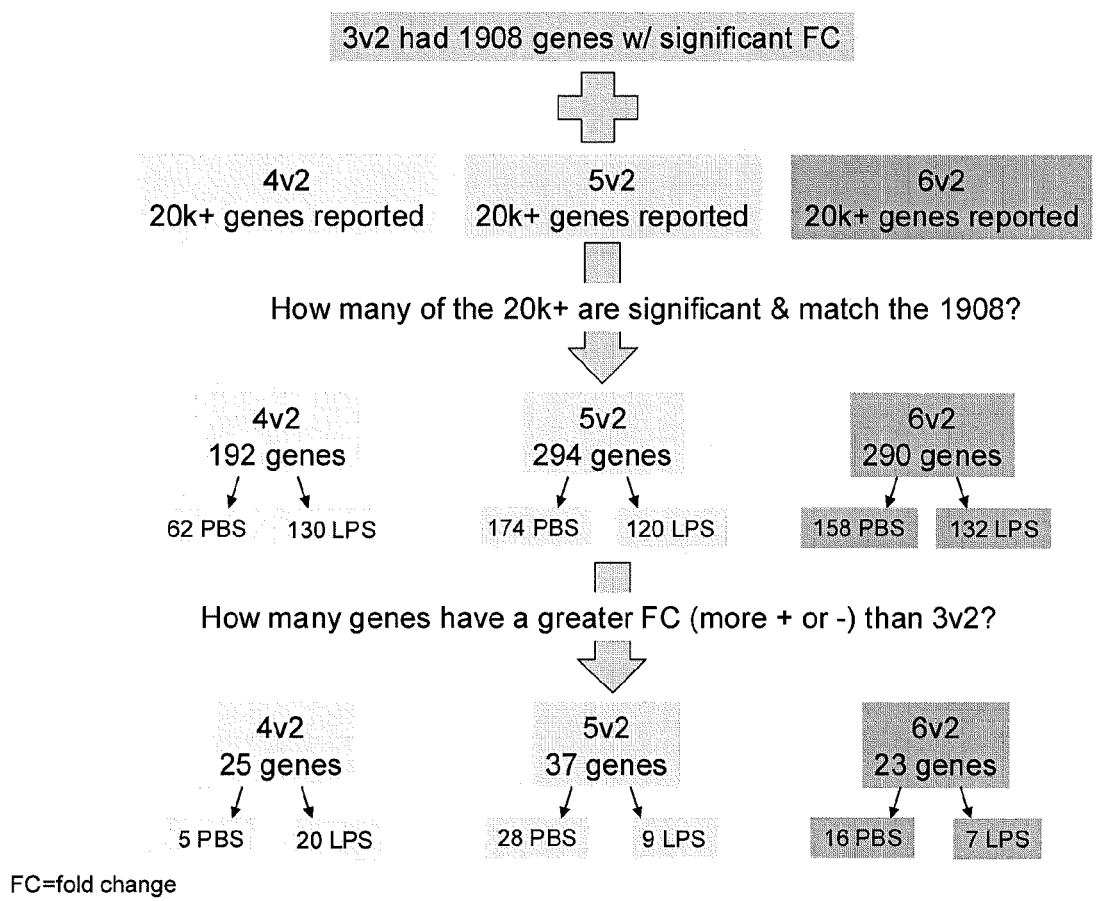
FIG. 1 depicts the analysis of PBS and LPS, all pairwise comparisons.

The reduced calorie infant formulas of the present disclosure include at least one nucleotide, at least one carotenoid, or a combination thereof. The reduced calorie infant formulas, which in some embodiments disclosed herein may additionally be low protein infant formulas, provide an infant with sufficient levels of carotenoids and/or nucleotides to provide an effective and simple means for reducing the incidence of long term adverse health effects in the infant, including for example obesity and cardiovascular disease, later in life.

The infant formulas provide the required nutritional benefits for growth and maturation to the infant, while providing the infant with the additional significant advantage of decreasing the incidence of long term adverse health effects, many of which continue to afflict more and more teenagers and adults everyday. These benefits, as well as other benefits as described herein are, advantageously, provided to the infant without any type of dietary change or specific dietary requirement. The infant formulas as described herein can provide infants with dependable, high quality nutrition, as well as program the infant early in life such that the infant has a head start to a healthy body shape and improved general overall health later in life. The infant formulas as described herein provide the infant with nutritional benefits early in life that transcend into significant health benefits later in life allowing the infant to potentially lead a longer, healthier life as a teenager and adult.

These and other and optional features of the infant formulas and methods of the present disclosure, as well as some of the many other optional variations and additions, are described in detail hereafter.

The terms "retort" and "retort sterilized" are used interchangeably herein, and unless otherwise specified, refer to the common practice of filling a container, most typically a metal can or other similar package, with a nutritional liquid, such as a liquid infant formula, and then subjecting the liquid-filled package to the necessary heat sterilization step, to form a retort sterilized nutritional liquid product.

The terms "aseptic" and "aseptic sterilized" are used interchangeably herein, and unless otherwise specified, refer to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "nutritional formula" or "nutritional product" or "nutritional composition," as used herein, are used interchangeably and, unless otherwise specified, refer to nutritional liquids, nutritional powders, nutritional solids, nutritional semi-liquids, semi-solids, nutritional supplements, nutritional tablets, and any other nutritional food product as known in the art. The nutritional powders may be reconstituted to form a nutritional liquid, all of which comprise one or more of fat, protein and carbohydrate, and are suitable for oral consumption by a human. Nutritional formulas may include infant formulas.

The term "nutritional liquid," as used herein, unless otherwise specified, refers to nutritional products in ready-to-drink liquid form, concentrated form, and nutritional liquids made by reconstituting the nutritional powders described herein prior to use.

The term "nutritional powder," as used herein, unless otherwise specified, refers to nutritional products in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "infant," as used herein, unless otherwise specified, refers to a child 12 months or younger. The term "preterm infant," as used herein, refers to an infant born prior to 36 weeks of gestation. The term "term infant," as used herein, refers to an infant born at or after 36 weeks of gestation.

The term "newborn infant," as used herein, unless otherwise specified, refers to infants less than about 3 months of age, including infants from zero to about 2 weeks of age. The newborn infant may be a term or preterm infant.

The term "infant formula," as used herein, unless otherwise specified, refers to liquid and solid nutritional products suitable for consumption by an infant. Unless otherwise specified herein, the term "infant formula" is intended to encompass both term and preterm infant formulas.

The term "preterm infant formula," as used herein, unless otherwise specified, refers to liquid and solid nutritional products suitable for consumption by a preterm infant.

The term "full calorie infant formula," as used herein, refers to an infant formula in which the caloric density or energy content of the formula has not been reduced from that conventionally included in infant formula. Typically, a full calorie infant formula will have an energy content of at least 650 kcal/L, including at least 660 kcal/L, and more typically at least 676 kcal/L, including 650 kcal/L to 800 kcal/L.

The term "reduced calorie infant formula," as used herein, refers to an infant formula that has a lower energy content, on a per volume basis, than a full calorie infant formula.

The term "later in life," as used herein, refers to the period of life from adolescence through adulthood.

The terms "susceptible to," and "at risk of," as used herein, are used interchangeably to refer to individuals having little resistance to a certain condition or disease, including being genetically predisposed, having a family history of, and/or having symptoms of the condition or disease The terms "inflammatory disease," "inflammatory-related disease," or "inflammatory condition" as used herein, unless otherwise specified, refer to any disease, disorder, or condition characterized by inflammation.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the infant formulas of the present disclosure may also be substantially free of any optional or selected essential ingredient or feature described herein, provided that the remaining infant formulas still contain all of the required ingredients or features as described herein. In this context, and unless otherwise specified, the term "substantially free" means that the selected infant formulas contain less than a functional amount of the optional ingredient, typically less than 1%, including less than 0.5%, including less than 0.1%, and also including zero percent, by weight of such optional or selected essential ingredient.

The infant formulas and methods of the present disclosure may comprise, consist of, or consist essentially of the essential elements of the products and methods as described herein, as well as any additional or optional element described herein or otherwise useful in nutritional infant formula applications.

Product Form

The infant formulas of the present disclosure may be formulated and administered in any known or otherwise suitable oral product form. Any solid, liquid, semi-solid, semi-liquid or powder form, including combinations or variations thereof, are suitable for use herein, provided that such forms allow for safe and effective oral delivery to the individual of the essential ingredients as also defined herein.

Specific non-limiting examples of product forms suitable for use with products and methods disclosed herein include, for example, liquid and powder preterm infant formulas, liquid and powder term infant formulas, and liquid and powder elemental and semi-elemental formulas.

The infant formulas of the present disclosure are desirably formulated as dietary product forms, which are defined herein as those embodiments comprising the ingredients of the present disclosure in a product form that then contains at least one of fat, protein, and carbohydrate.

The infant formulas may be formulated with sufficient kinds and amounts of nutrients to provide a sole, primary, or supplemental source of nutrition, or to provide a specialized nutritional product for use in infants afflicted with specific diseases or conditions or with a targeted nutritional benefit.

Desirably, the infant formulas of the present disclosure are formulated for both term and preterm infants. Desirably, the infant formula is formulated for feeding to infants within the first few days, weeks, or months following birth, and including for feeding to infants from age zero to one year, including zero to six months, including zero to four months, and including zero to two months. In some embodiments the infant formulas are for feeding to newborn infants in the first few weeks of life, including birth to four weeks of life, including birth to three weeks of life, including birth to two weeks of life, and including birth to the first week of life. It is to be understood that the administration of the infant formulas of the present disclosure is not limited to administration during only the first six months following birth, but may be administered to older infants as well.

Nutritional Liquids

Nutritional liquids include both concentrated and ready-to-feed nutritional liquids. These nutritional liquids are most typically formulated as suspensions, emulsions or clear or substantially clear liquids.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional liquids may be and typically are shelf stable. The nutritional liquids typically contain up to about 95% by weight of water, including from about 50% to about 95%, also including from about 60% to about 90%, and also including from about 70% to about 85%, of water by weight of the nutritional liquid. The nutritional liquids may have a variety of product densities, but most typically have a density about 1.01 g/mL or higher, including greater than about 1.02 g/mL, including greater than about 1.03 g/mL, including greater than about 1.04 g/mL, including greater than about 1.055 g/mL, including from about 1.06 g/mL to about 1.12 g/mL, and also including from about 1.085 g/mL to about 1.10 g/mL.

The nutritional liquid may have a pH ranging from about 3.5 to about 8, but is generally most advantageously in a range of from about 4.5 to about 7.5, including from about 4.5 to about 7.0, including from about 4.5 to about 6.5, including from about 4.5 to about 6.0. In other embodiments, the pH range may be from about 5.5 to about 7.3, including from about 5.5 to about 7.0, including from about 5.5 to about 6.5, including from about 6.2 to about 7.2, including from about 6.2 to about 7.0, and including from about 6.2 to about 6.5.

Although the serving size for the nutritional liquid can vary depending upon a number of variables, a typical serving size is generally at least about 2 mL, or even at least about 5 mL, or even at least about 10 mL, or even at least about 25 mL, including ranges from about 2 mL to about 300 mL, including from about 100 mL to about 300 mL, from about 4 mL to about 250 mL, from about 150 mL to about 250 mL, from about 10 mL to about 240 mL, and from about 190 mL to about 240 mL.

Nutritional Powders

The nutritional powders are in the form of flowable or substantially flowable particulate compositions, or at least particulate compositions. Particularly suitable nutritional powder forms include spray dried, agglomerated or dry-blended powder compositions, or combinations thereof, or powders prepared by other suitable methods. The compositions can easily be scooped and measured with a spoon or similar other device, wherein the compositions can easily be reconstituted with a suitable aqueous liquid, typically water, to form a nutritional liquid, such as an infant formula, for immediate oral or enteral use. In this context, "immediate" use generally means within about 48 hours, most typically within about 24 hours, preferably right after or within 20 minutes of reconstitution.

Energy Content of Infant Formula

The infant formulas of the present disclosure have a reduced energy content (used herein interchangeably with the term "caloric density") relative to conventional term and preterm infant formulas. The reduced energy density of the infant formulas can, in combination with specific components of the formula including carotenoids and/or nucleotides as described herein, aid in the reduction of long term adverse health effects as noted below. The reduced energy content may, in some embodiments, be achieved by reducing the level of one or more macronutrients in the formula. Specifically, the infant formulas of the present disclosure provide a caloric density or energy content of less than 650 kcal/L, including from about 200 kcal/L to less than 650 kcal/L, including from about 200 kcal/L to about 600 kcal/L, and more particularly from about 250 kcal/L to about 500 kcal/L. In some embodiments, the caloric density may be between about 250 kcal/L and about 450 kcal/L, or even from about 250 kcal/L and about 400 kcal/L, or even from about 250 kcal/L to about 300 kcal/L. In contrast to the infant formulas of the present disclosure, the caloric density or energy content of conventional term and preterm infant formulas, which are also referred to herein as "full calorie infant formulas," is significantly higher, typically ranging from 650 kcal/L to 880 kcal/L.

When the infant formulas of the present disclosure are in powder form, then the powder is intended for reconstitution prior to use to obtain the above-noted caloric densities and other nutrient requirements. Likewise, when the infant formulas of the present disclosure are in a concentrated liquid form, then the concentrate is intended for dilution prior to use to obtain the requisite caloric densities and nutrient requirements. The infant formulas can also be formulated as ready-to-feed liquids already having the requisite caloric densities and nutrient requirements.

The infant formulas of the present disclosure are desirably administered to infants, and in particular newborn infants, in accordance with the methods described herein. Such methods may include feedings with the infant formulas in accordance with the daily formula intake volumes described herein.

The energy component of the infant formula is most typically provided by a combination of fat, protein, and carbohydrate nutrients. In some embodiments, the protein may comprise from about 4% to about 40% of the total calories, including from about 10% to about 30%, also including from about 15% to about 25%; the carbohydrate may comprise less than 50% of the total calories, including from about 5% to about 45%, also including less than about 42%, and also including from about 20% to about 37%; and the fat may comprise the remainder of the formula calories, most typically less than about 60% of the calories, including from about 30% to about 60%. Other exemplary amounts of protein, carbohydrate, and fat are set forth hereinafter for use in alternative embodiments.

Nucleotides

The infant formulas of the present disclosure may comprise one or more nucleotides, alone or in combination with other nutritional components as described herein, to reduce the long term adverse health effects in an individual, including long term obesity. "Nucleotides" as used herein includes nucleotides, nucleosides, nucleobases, and combinations thereof, unless otherwise specified in a particular embodiment. Suitable nucleotides may be selected from the group consisting of nucleosides, purine bases, pyrimidine bases, ribose and deoxyribose. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the infant formula as a free acid or in the form of a salt, preferably a monosodium salt.

Additional suitable nucleotides and/or nucleosides for use in the nutritional compositions include one or more of 3'-deoxyadenosine, cytidine 5'-monophosphate, uridine 5'-monophosphate, adenosine 5'-monophosphate, guanosine 5'-1-monophosphate, and/or adenosine 5'-monophosphate, more preferably cytidine 5'-monophosphate, uridine 5'-monophosphate, adenosine 5'-monophosphate, guanosine 5'-monophosphate, and adenosine 5'-monophosphate. In some embodiments, the nucleotides are in free form and include adenine, cytosine, uracil, guanine, and thymine. Some particularly preferred nucleotides include cytidine 5' monophosphate, disodium guanosine 5' monophosphate, disodium uridine 5' monophosphate, and adenosine 5' monophosphate. Any of these particularly preferred nucleotides may be used alone, in a combination.

The nucleotide is present in the infant formulas in total amounts of nucleotides of at least about 10 mg/L, including from about 10 mg/L to about 200 mg/L, including from about 10 mg/L to about 150 mg/L, including from about 10 mg/L to about 125 mg/L, including from about 42 mg/L to about 102 mg/L, and including at least about 72 mg/L of the infant formula.

In one specific embodiment when the infant formula is a nutritional powder, the nucleotide may be present at a level of at least about 0.007%, including from about 0.0078% to about 0.1556%, and including about 0.056% (by weight of the nutritional powder), or at least about 0.007 grams, including from about 0.0078 grams to about 0.1556 grams, and including about 0.056 grams of nucleotide per 100 grams of nutritional powder.

In another specific embodiment, when the infant formula is a ready-to-feed nutritional liquid, the nucleotide is present at a level of at least about 0.001%, including from about 0.001% to about 0.0197%, and including about 0.0071% (by weight of the nutritional liquid), or at least about 0.001 grams, including from about 0.001 grams to about 0.0197 grams, and including about 0.0071 grams of nucleotide per 100 grams of ready-to-feed nutritional liquid.

In another specific embodiment when the infant formula is a concentrated nutritional liquid, the nucleotide is present at a level of at least about 0.0019%, including from about 0.0019% to about 0.0382%, and including about 0.0138% (by weight of the nutritional liquid), or at least about 0.0019 grams, including from about 0.0019 grams to about 0.0382 grams, and including about 0.0138 grams of nucleotide per 100 grams of concentrated nutritional liquid.

Carotenoids

The infant formulas of the present disclosure may include a carotenoid alone or in combination with other nutritional components as described herein, including a nucleotide, to reduce the long term adverse health effects in an individual, including long term obesity. The carotenoid may include one or more carotenoids, and particularly, combinations of the carotenoids lutein, lycopene, zeaxanthin and/or beta-carotene.

It is generally preferable that the infant formulas comprise at least one of lutein, lycopene, zeaxanthin, beta-carotene to provide a total amount of carotenoid of from about 0.001 mg/L to about 5 mg/L, including from about 0.01 mg/L to about 1 mg/L, and including from about 0.1 mg/L to about 0.5 mg/L. More particularly, the infant formulas comprise lutein in an amount of from 0.001 μg/mL to 5 μg/mL, including from 0.001 μg/mL to 0.500 μg/mL, including from 0.01 μg/mL to 0.250 μg/mL, including from 0.025 μg/mL to 0.20 μg/L, and also including from 0.044 μg/mL to 5 μg/mL of lutein. It is also generally preferable that the infant formulas comprise from 0.001 μg/mL to 5 μg/mL, including from 0.01 μg/mL to 0.500 μg/mL, including from 0.05 μg/mL to 0.250 μg/mL, including from 0.055 μg/mL to 0.130 μg/mL of lycopene, and also including from 0.0185 μg/L to 5 μg/L of lycopene. It is also generally preferable that the infant formulas comprise from 0.001 μg/mL to 5 μg/mL, including from 0.001 μg/mL to 0.500 μg/mL, including from 0.01 μg/mL to 0.300 μg/L of beta-carotene, including from 0.025 μg/L to 0.200 μg/mL of beta-carotene, and also including from 0.034 μg/mL to about 5 μg/mL of beta-carotene. It should be understood that any combination of these amounts of beta-carotene, lutein, zeaxanthin, and lycopene can be included in the infant formulas of the present disclosure. Other carotenoids may optionally be included in the infant formulas as described herein. Any one or all of the carotenoids included in the infant formulas described herein may be from a natural source, or artificially synthesized.

Each of the carotenoids in the selected combinations can be obtained from any known or otherwise suitable material source for use in infant formulas, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LycoVit® lycopene (available from BASF, Mount Olive, N.J.), Lyc-O-Mato® tomato extract in oil, powder, or bead form (available from LycoRed Corp., Orange, N.J.), beta-carotene, lutein, or lycopene (available from DSM Nutritional Products, Parsippany, N.J.), Flora-GLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J.).

Macronutrients

The low calorie infant formulas of the present disclosure may further comprise one or more macronutrient, in addition to the nucleotides and/or carotenoids described herein. The macronutrients include protein, fat, carbohydrate, and combinations thereof. Macronutrients suitable for use herein include any protein, fat, carbohydrate, or source thereof that is known for or otherwise suitable for use in an oral nutritional product, provided that the macronutrient is safe and effective for oral administration to infants and is otherwise compatible with the other ingredients in the infant formula. The macronutrients described herein can be adjusted as necessary by one skilled in the art based on the disclosure herein to obtain the desired caloric density and protein level.

Although total concentrations or amounts of the protein, fat, and carbohydrate may vary depending upon the product form (e.g., powder or ready-to-feed liquid) and targeted dietary needs of the intended user, such concentrations or amounts most typically fall within one of the embodied ranges described in the following table (each numerical value is preceded by the term "about"), inclusive of any other essential fat, protein, and or carbohydrate ingredients as described herein. For powder embodiments, the amounts in the following Table A are amounts following reconstitution of the powder.

TABLE A

| Nutrient (g/100 mL) | Example A | Example B |
| --- | --- | --- |
| Protein | 0.5 to 1.5 | 0.6 to 0.9 |
| Fat | 1.2 to 2.5 | 1.4 to 2.3 |
| Carbohydrate | 2.7 to 6.5 | 3.1 to 6.1 |

The level or amount of carbohydrate, fat, and protein in the infant formula (whether a powder formula or a liquid ready-to-feed or concentrated liquid) may also be characterized in addition to or in the alternative as a percentage of total calories in the infant formulas. These macronutrients for infant formulas of the present disclosure are most typically formulated within any of the caloric ranges described in the following Table B (each numerical value is preceded by the term "about").

TABLE B

| Nutrient (% total calories) | Example C | Example D | Example E |
| --- | --- | --- | --- |
| Carbohydrate | 2 to 96 | 10 to 75 | 30 to 50 |
| Protein | 2 to 96 | 5 to 70 | 15 to 35 |
| Fat | 2 to 96 | 20 to 85 | 35 to 55 |
|  | Example F | Example G | Example H |
| Carbohydrate | 25 to 50 | 25 to 50 | 35 to 50 |
| Protein | 10 to 30 | 5 to 30 | 7.5 to 25 |
| Fat | 1 to 20 | 2 to 20 | 30 to 60 |

Protein

The infant formulas of the present disclosure may comprise protein in addition to the nucleotides and/or carotenoids described herein. Any known or otherwise suitable protein or protein source may be included in the infant formulas of the present disclosure, provided that such proteins are suitable for feeding to infants, and in particular, newborn infants.

Non-limiting examples of suitable protein or sources thereof for use in the infant formulas include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy), or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. The proteins for use herein can also include, or be entirely or partially replaced by, free amino acids known for use in nutritional products, non-limiting examples of which include L-alanine, L-aspartic acid, L-glutamic acid, glycine, L-histidine, L-isoleucine, L-leucine, L-phenylalanine, L-proline, L-serine, L-threonine, L-valine, L-tryptophan, L-glutamine, L-tyrosine, L-methionine, L-cysteine, taurine, L-arginine, L-carnitine, and combinations thereof. Particularly preferred protein sources for use in the infant formulas described herein include non-fat milk and whey protein concentrate. In a particularly preferred embodiment, the non-fat milk and whey protein concentrate is used in combination in the infant formula.

In some embodiments the infant formulas of the present disclosure include reduced amounts of protein as compared to conventional term and preterm infant formulas. For example, the reduced protein infant formulas include protein in an amount of less than 14.0 grams protein per liter of formula, including from about 5.0 to about 10.0 grams protein per liter of formula, and including from about 7.6 to about 10.0 grams protein per liter of formula.

Fat

The infant formulas of the present disclosure may comprise a source or sources of fat in addition to the nucleotides and/or carotenoids described herein. Suitable sources of fat for use in the infant formulas disclosed herein include any fat or fat source that is suitable for use in an oral nutritional product and is compatible with the essential elements and features of such products, provided that such fats are suitable for feeding to infants.

Non-limiting examples of suitable fats or sources thereof for use in the infant formulas described herein include coconut oil, fractionated coconut oil, soybean oil, corn oil, olive oil, safflower oil, high oleic safflower oil, high GLA-safflower oil, oleic acids, MCT oil (medium chain triglycerides), sunflower oil, high oleic sunflower oil, structured triglycerides, palm and palm kernel oils, palm olein, canola oil, flaxseed oil, borage oil, evening primrose oil, blackcurrant seed oil, transgenic oil sources, marine oils (e.g., tuna, sardine), fish oils, fungal oils, algae oils, cottonseed oils, and combinations thereof. In one embodiment, suitable fats or sources thereof include oils and oil blends including long chain polyunsaturated fatty acids (LC-PUFAs). Some non-limiting specific polyunsaturated acids for inclusion include, for example, docosahexaenoic acid (DHA), arachidonic acid (ARA), eicosapentaenoic acid (EPA), linoleic acid (LA), and the like. Non-limiting sources of arachidonic acid and docosahexaenoic acid include marine oil, egg derived oils, fungal oil, algal oil, and combinations thereof. Particularly preferred fat sources include high oleic safflower oil, soy oil, and coconut oils, which may all be used in combination with ARA and/or DHA oil. In one preferred embodiment, the infant formula included a combination of high oleic safflower oil, soy oil, and coconut oil, in combination with ARA oil and DHA oil.

Carbohydrate

The infant formulas of the present disclosure may comprise any carbohydrates that are suitable for use in an oral nutritional product, such as an infant formula, and are compatible with the essential elements and features of such product.

Non-limiting examples of suitable carbohydrates or sources thereof for use in the infant formulas described herein may include maltodextrin, hydrolyzed, intact, or modified starch or cornstarch, glucose polymers, corn syrup, corn syrup solids, rice-derived carbohydrates, rice syrup, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia), indigestible oligosaccharides such as fructooligosaccharides (FOS), and combinations thereof. In one embodiment, the carbohydrate may include a maltodextrin having a DE value of less than 20. One preferred carbohydrate is lactose.

Other Optional Ingredients

The infant formulas of the present disclosure may further comprise other optional ingredients that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, anti-oxidants, emulsifying agents, buffers, fructooligosaccharides, galactooligosaccharides, human milk oligosaccharides and other prebiotics, pharmaceutical actives, additional nutrients as described herein, colorants, flavors, thickening agents and stabilizers, emulsifying agents, lubricants, and so forth, and combinations thereof.

A flowing agent or anti-caking agent may be included in the powder infant formulas as described herein to retard clumping or caking of the powder over time and to make a powder embodiment flow easily from its container. Any known flowing or anti-caking agents that are known or otherwise suitable for use in a nutritional powder or product form are suitable for use herein, non limiting examples of which include tricalcium phosphate, silicates, and combinations thereof. The concentration of the flowing agent or anti-caking agent in the nutritional product varies depending upon the product form, the other selected ingredients, the desired flow properties, and so forth, but most typically range from about 0.1% to about 4%, including from about 0.5% to about 2%, by weight of the composition.

A stabilizer may also be included in the infant formulas. Any stabilizer that is known or otherwise suitable for use in a nutritional product is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the infant formula.

Methods of Manufacture

The infant formulas of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the infant formulas described herein.

The infant formulas of the present disclosure can therefore be prepared by any of a variety of known or otherwise effective formulation or manufacturing methods. In one suitable manufacturing process, for example, at least two separate slurries are prepared, that are later blended together, heat treated, standardized, and either terminally sterilized to form a retort infant formula or aseptically processed and filled to form an aseptic infant formula. Alternately, the slurries can be blended together, heat treated, standardized, heat treated a second time, evaporated to remove water, and spray dried to form a powder infant formula.

The slurries formed may include a carbohydrate-mineral (CHO-MIN) slurry and a protein-in-fat (PIF) slurry. Initially, the CHO-MIN slurry is formed by dissolving selected carbohydrates (e.g., lactose, galactooligosaccharides, etc.) in heated water with agitation, followed by the addition of minerals (e.g., potassium citrate, magnesium chloride, potassium chloride, sodium chloride, choline chloride, etc.). The resulting CHO-MIN slurry is held with continued heat and moderate agitation until it is later blended with the other prepared slurries.

The PIF slurry is formed by heating and mixing the oil (e.g., high oleic safflower oil, soybean oil, coconut oil, monoglycerides, etc.) and emulsifier (e.g., soy lecithin), and then adding oil soluble vitamins, mixed carotenoids, protein (e.g., milk protein concentrate, milk protein hydrolysate, etc.), carrageenan (if any), calcium carbonate or tricalcium phosphate (if any), and ARA oil and DHA oil (in some embodiments) with continued heat and agitation. The resulting PIF slurry is held with continued heat and moderate agitation until it is later blended with the other prepared slurries.

Water was heated and then combined with the CHO-MIN slurry, nonfat milk (if any), and the PIF slurry under adequate agitation. The pH of the resulting blend was adjusted to 6.6-7.0, and the blend was held under moderate heated agitation. ARA oil and DHA oil is added at this stage in some embodiments.

The composition is then subjected to high-temperature short-time (HTST) processing, during which the composition is heat treated, emulsified and homogenized, and then cooled. Water soluble vitamins, any trace minerals and ascorbic acid are added, the pH is adjusted to the desired range if necessary, flavors (if any) are added, and water is added to achieve the desired total solid level. For aseptic infant formulas, the emulsion receives a second heat treatment through an aseptic processor, is cooled, and then aseptically packaged into suitable containers. For retort infant formulas, the emulsion is packaged into suitable containers and terminally sterilized. In some embodiments, the emulsions can be optionally further diluted, heat-treated, and packaged to form a desired ready-to-feed or concentrated liquid, or can be heat-treated and subsequently processed and packaged as a reconstitutable powder, e.g., spray dried, dry mixed, agglomerated.

The spray dried powder infant formula or dry-mixed powder infant formula may be prepared by any collection of known or otherwise effective techniques, suitable for making and formulating a nutritional powder. For example, when the powder infant formula is a spray-dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried powder infant formulas herein. Following drying, the finished powder may be packaged into suitable containers.

Methods of Use

The reduced calorie infant formulas and the reduced calorie and reduced protein infant formulas of the present disclosure may be orally administered to infants, including term, preterm, and/or newborn infants. The reduced calorie infant formulas may be administered as a source of nutrition for infants and/or can be used to prevent and/or reduce and/or minimize and/or eliminate the development and/or onset of one or more of the potentially inflammatory-related diseases or conditions later in life as discussed herein. One subclass of general infant population that can effectively utilize the infant formulas described herein include those infants that are susceptible to, or at risk of, getting one or more the diseases or conditions (is at elevated risk as compared to the general infant population for getting the disease or condition due to certain conditions including family history, etc.) described herein, including obesity, later in life. These infants who are susceptible to or at risk of getting the disease or condition may be referred to as "in need of" assistance (or "in need thereof" as referring to the assistance needed) in combating getting the disease or condition later in life. The methods of the present disclosure are particularly directed to infants that have a family history of the diseases and conditions set forth herein, and particularly a family history of obesity or diabetes or insulin control problems, as family history is highly indicative of what diseases/conditions an individual may expect to face later in life.

Based on the forgoing, because some of the method embodiments of the present disclosure are directed to specific subsets or subclasses of infants (that is, the subset or subclass of infants that are "in need" of assistance in addressing one or more specific diseases or specific conditions that they are susceptible to later in life), not all infants can benefit from all method embodiments described herein as not all infants will fall within the subset or subclass of infants as described herein for certain diseases or conditions.

The infant formulas will typically be administered daily, at intake volumes suitable for the age of the infant. For instance, the methods of the present disclosure may include administering one or more of the reduced calorie or reduced calorie/reduced protein formulas of the present disclosure to an infant at the average intake volumes described herein. In some embodiments, newborn infants are provided with increasing formula volumes during the initial weeks of life. Such volumes most typically range up to about 100 mL/day on average during the first day or so of life; up to about 200 to about 700 mL/day, including from about 200 to about 600 mL/day, and also including from about 250 to about 500 mL/day, on average during the remainder of the three month newborn feeding period. It is to be understood, however, that such volumes can vary considerably depending upon the particular newborn infant and their unique nutritional needs during the initial weeks or months of life, as well as the specific nutrients and caloric density of the infant formula administered.

In some embodiments, the methods of the present disclosure may be directed to infants during the initial days, weeks or months of life. Desirably, the low calorie infant formulas described herein are administered to the infant for a duration of at least the first week of life, more desirably during at least the first two weeks of life, more desirably during at least the first one or two months of life, more desirably during at least the first four months of life, and more desirably during at least the first six months of life, and including up to the first year of life. Thereafter, the infant may be switched to a conventional infant formula, alone or in combination with human milk. It should be understood by one skilled in the art based on the disclosure herein that the infant formulas described herein can be used alone, or in combination with human breast milk, or in combination with other infant formulas.

The infant formulas used in the methods described herein, unless otherwise specified, are nutritional formulas and may be in any product form, including ready-to-feed liquids, concentrated liquids, reconstituted powders, and the like as described above. In embodiments where the infant formulas are in powder form, the method may further comprise reconstituting the powder with an aqueous vehicle, most typically water or human milk, to form the desired caloric density, which is then orally or enterally fed to the infant. The powdered formulas are reconstituted with a sufficient quantity of water or other suitable fluid such as human milk to produce the desired caloric density, as well as the desired feeding volume suitable for one infant feeding. The infant formulas may also be sterilized prior to use through retort or aseptic means.

In one aspect, the present disclosure is directed to a method of providing nutrition to an infant. The method comprises administering to the infant any one or more of the reduced calorie infant formulas of the present disclosure. Such methods may include the daily administration of the infant formulas, including administration at the daily intake volumes as described hereinbefore. In some embodiments, the infant is a newborn infant.

In another aspect, the infant formulas can be administered to the infant as described herein to reduce one or more long term adverse health effects later in the life of the infant. Particularly, in some embodiments, the infant formulas can be administered in amounts such to decrease the expression of proinflammatory cytokines and to increase anti-inflammatory cytokines early in life and later in life. Further, administration of these formulas inhibits inflammatory pathways such as NF-κB and MAPK, thereby reducing inflammation. By reducing inflammation, which may be an underlying mechanism of inflammatory-related diseases and conditions, the risk of the infants getting the diseases later in life is reduced and possibly even prevented in some embodiments. The infant formulas of the present disclosure are intended to be utilized in some embodiments to reduce or eliminate later in life as discussed herein specific adverse health effects including obesity, type 2 diabetes, insulin resistance, non-insulin dependent diabetes mellitus, cardiovascular disease, and atherosclerosis.

EXAMPLES

The following examples illustrate specific embodiments and/or features of the infant formulas and methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

Unless otherwise specified, the retort sterilized formulas may be prepared in accordance with the manufacturing methods described herein, are ready-to-feed liquid formulas.

Examples 1-3

In these examples, 2 oz. retort sterilized infant formulas are prepared. The ingredients that may be used to prepare the formulas are set forth in Tables 1 and 2 below. The amounts of ingredients are amounts per 1000 kg batch.

TABLE 1

|  | Units | Formula 1 | Formula 2 |
|---|---|---|---|
| Energy | Kcal/L | 270 | 250 |
| Water | kg | Q.S. | Q.S. |
| Lactose | kg | 23.8 | 15.2 |
| Nonfat Milk | kg | 11.0 | 11.3 |

TABLE 1-continued

|  | Units | Formula 1 | Formula 2 |
|---|---|---|---|
| Galactooligosaccharides | kg | 4.40 | 4.40 |
| High Oleic Safflower Oil | kg | 5.33 | 5.37 |
| Soy Oil | kg | 3.99 | 4.00 |
| Coconut Oil | kg | 3.81 | 3.84 |
| Whey Protein Concentrate | kg | 2.79 | 2.86 |
| 1N KOH | g | 1060 | 1340 |
| Potassium Hydroxide | g | 53.0 | 67.0 |
| Calcium Phosphate Dibasic | g | — | 770.2 |
| Tricalcium Phosphate | g | 84.1 | — |
| Potassium Citrate | g | 1.24 | 1240 |
| Calcium Citrate | g | 131.3 | 768.9 |
| Ascorbic Acid | g | 485.0 | 727.5 |
| ARA Oil | g | 375.5 | 367.9 |
| Nucleotide-Choline Premix | g | 328.5 | 328.5 |
| Cytidine 5'-Monophosphate | g | 34.2 | 34.2 |
| Disodium Guanosine 5'-Monophosphate | g | 17.5 | 17.5 |
| Disodium Uridine 5'-Monophosphate | g | 14.7 | 14.7 |
| Adenosine 5'-Monophosphate | g | 13.0 | 13.0 |
| Magnesium Chloride | g | 88.4 | 450.7 |
| Sodium Chloride | g | 15.8 | 186.7 |
| Soy Lecithin | g | 143.0 | 143.0 |
| Distilled Monoglycerides | g | 143.0 | 143.0 |
| Vitamin/Mineral/Taurine Premix | g | 66.1 | 157.0 |
| Taurine | g | 20.2 | 48.0 |
| m-Inositol | g | 14.7 | 34.85 |
| Zinc Sulfate | g | 6.77 | 16.07 |
| Niacinamide | g | 4.31 | 10.24 |
| Calcium Pantothenate | g | 2.59 | 6.14 |
| Ferrous Sulfate | g | 2.263 | 5.37 |
| Cupric Sulfate | mg | 793.6 | 1890 |
| Thiamine Chloride HCL | mg | 669.3 | 1590 |
| Riboflavin | mg | 295 | 701 |
| Pyridoxine HCL | mg | 270.4 | 642 |
| Folic Acid | mg | 90.9 | 216 |
| Manganese Sulfate | mg | 77.0 | 183 |
| Biotin | mg | 26.1 | 62.0 |
| Sodium Selenate | mg | 15.7 | 37 |
| Cyanocobalamin | mg | 2.08 | 4.95 |
| DHA Oil | g | 140.7 | 137.9 |
| Potassium Chloride | g | 32.7 | 60.7 |
| Choline Chloride | g | 21.5 | 54.0 |
| Ferrous Sulfate | g | 26.9 | 60.9 |
| Carrageenan | g | 175.0 | 175.0 |
| Vitamin A, D3, E, K1 | g | 20.1 | 47.5 |
| RRR α-Tocopherol Acetate | g | 4.06 | 9.6 |
| Vitamin A Palmitate | mg | 763 | 1800 |
| Vitamin K1 | mg | 44.2 | 104.5 |
| Vitamin D3 | mg | 5.35 | 12.65 |
| Citric Acid | g | — | 29.8 |
| Mixed Carotenoid Premix | g | 23.8 | 23.8 |
| Lycopene | mg | 119 | 119 |
| Lutein | mg | 50 | 50 |
| Beta-carotene | mg | 26.2 | 26.2 |
| Inositol | g | 1.43 | 12.9 |
| L-Carnitine | g | 1.87 | 3.28 |
| Riboflavin | mg | 386 | 882 |

TABLE 2

|  | Units | Formula 3 |
|---|---|---|
| Energy | Kcal/L | 643 |
| Ingredient Water | Kg | Q.S. |
| Lactose | Kg | 51.22 |
| Nonfat Milk | Kg | 24.70 |
| High Oleic Safflower Oil | Kg | 12.94 |
| Soy Oil | Kg | 10.40 |
| Coconut Oil | Kg | 9.169 |
| Galacto-oligosaccharides | Kg | 8.630 |
| Whey Protein Concentrate | Kg | 6.075 |
| 1N KOH | Kg | 4.060 |

TABLE 2-continued

| | Units | Formula 3 |
|---|---|---|
| Potassium Hydroxide | g | 203.0 |
| Ascorbic Acid | g | 727.5 |
| Calcium Carbonate | g | 511.6 |
| Potassium Citrate | g | 509.2 |
| Soy Lecithin | g | 508.4 |
| Distilled Monoglycerides | g | 508.4 |
| ARA Oil | g | 359.3 |
| Nucleotide-Choline Premix | g | 293.2 |
| Choline Bitartrate | g | 51.75 |
| Cytidine 5'-Monophosphate | g | 30.49 |
| Disodium Guanosine 5'-Monophosphate | g | 15.64 |
| Disodium Uridine 5'-Monophosphate | g | 13.15 |
| Adenosine 5'-Monophosphate | g | 11.60 |
| Potassium Chloride | g | 227.3 |
| Carrageenan | g | 175.0 |
| Vit/Min/Taur Premix | g | 149.9 |
| Taurine | g | 45.83 |
| m-Inositol | g | 33.28 |
| Zinc Sulfate | g | 15.35 |
| Niacinamide | g | 9.781 |
| Calcium Pantothenate | g | 5.865 |
| Ferrous Sulfate | g | 5.131 |
| Cupric Sulfate | g | 1.800 |
| Thiamine Chloride HCl | g | 1.518 |
| Riboflavin | mg | 669.3 |
| Pyridoxine HCl | mg | 613.1 |
| Folic Acid | mg | 206.1 |
| Manganese Sulfate | mg | 174.6 |
| Biotin | mg | 59.21 |
| Sodium Selenate | mg | 35.51 |
| Cyanocobalamin | mg | 4.722 |
| Magnesium Chloride | g | 148.4 |
| DHA Oil | g | 131.0 |
| Vitamin A, D3, E, K1 | g | 69.36 |
| RRR Alpha-Tocopheryl Acetate | g | 8.986 |
| Vitamin A Palmitate | g | 1.783 |
| Vitamin K1 (Phylloquinone) | mg | 99.50 |
| Vitamin D3 | mg | 13.87 |
| Choline Chloride | g | 65.41 |
| Ferrous Sulfate | g | 60.91 |
| Carotenoid Premix | g | 57.14 |
| Lutein | mg | 120.0 |
| Lycopene | mg | 119.0 |
| Beta-Carotene | mg | 26.17 |
| Ultra-Micronized Tricalcium Phosphate | g | 34.28 |
| Potassium Phosphate Monobasic | g | 30.10 |
| Citric Acid (Processing Aid) | g | 29.88 |
| L-Carnitine | g | 3.616 |
| Riboflavin | g | 1.166 |
| Sodium Chloride | g | as needed |

The formulas were prepared by making at least two separate slurries that were later blended together, heat treated, standardized, and terminally sterilized. Initially, a carbohydrate-mineral slurry was prepared by dissolving the selected carbohydrates (e.g. lactose, galactooligosaccharides) in water at 74-79° C., followed by the addition of citric acid, magnesium chloride, potassium chloride, potassium citrate, choline chloride, and sodium chloride. The resulting slurry was held under moderate agitation at 49-60° C. until it was later blended with the other prepared slurries.

A protein-in-fat slurry was prepared by combining the high oleic safflower oil, coconut oil, monoglycerides, and soy lecithin under agitation and heating to 66-79° C. Following a 10-15 minute hold time, soybean oil, oil soluble vitamin premix, mixed carotenoid premix, carrageenan, vitamin A, calcium citrate, dicalcium phosphate, ARA oil, DHA oil, and whey protein concentrate were then added to the slurry. The resulting oil slurry was held under moderate agitation at 49-60° C. until it was later blended with the other prepared slurries.

Water was heated to 49-60° C. and then combined with the carbohydrate-mineral slurry, nonfat milk, and the protein-in-fat slurry under adequate agitation. The pH of the resulting blend was adjusted with potassium hydroxide. This blend was held under moderate agitation at 49-60° C.

The resulting blend was heated to 74-79° C., emulsified through a single stage homogenizer to 900-1100 psig, and then heated to 144-147° C., for about 5 seconds. The heated blend was passed through a flash cooler to reduce the temperature to 88-93° C. and then through a plate cooler to further reduce the temperature to 74-85° C. The cooled blend was then homogenized at 2900-3100/400-600 psig, held at 74-85° C. for 16 seconds, and then cooled to 2-7° C. Samples were taken for analytical testing. The mixture was held under agitation at 2-7° C.

A water-soluble vitamin (WSV) solution and an ascorbic acid solution were prepared separately and added to the processed blended slurry. The vitamin solution was prepared by adding the following ingredients to water with agitation: potassium citrate, ferrous sulfate, WSV premix, L-carnitine, copper sulfate, riboflavin, inositol, and the nucleotide-choline premix. The ascorbic acid solution was prepared by adding potassium hydroxide and ascorbic acid to a sufficient amount of water to dissolve the ingredients. The ascorbic acid solution pH was then adjusted to 5-9 with potassium hydroxide.

The blend pH was adjusted to a specified pH range of 7.1-7.6 with potassium hydroxide (varied by product) to achieve optimal product stability. The completed product was then filled into suitable containers and thermally sterilized.

Example 4

Methods 8 week old male C57BL6/J mice (ordered from Jackson Labs, Bar Harbor, Me.) were singled housed and allowed a 1 week acclimation to the facility and control diet prior to the start of the study. Mice were randomly assigned to one of 6 dietary groups as follows (n=8 mice per diet group)

1. D12450B: Control diet
2. D11083104: Control diet+nucleotides+carotenoids
3. D11083101: Nutrient restriction
4. D11083102: Calorie restriction+nucleotides
5. D11083103: Calorie restriction+carotenoids
6. D11083104: Calorie restriction+nucleotides+carotenoids Diets were formulated by Research Diets, Inc. New Brunswick N.J. according to the specifications set forth in Table 3. Diets were tested for compounds of interests at Abbott Nutrition prior to delivery to University of Illinois, Urbana Champaign (UIUC).

Mice in the control group were fed ad libitum with daily (Monday-Saturday with a two day allotment of food provided on Saturday) weighing and recording of food intake. All experiment feeding groups (3-6) received 90%, by weight, of the average daily intake of the control group (1). Experimental diets (3-6) were given daily by removing any food in the hopper or visible in the bedding and replaced with 90%, by weight, of control diet. Cages were cleaned and changed weekly. For purposes of tissue collection, feeding was staggered within one week.

After 30 days of feeding, mice were treated with Lipopolysaccharide ("LPS") (100 µg/kg) or Phosphate Buffered Saline ("PBS") (volume matched) via i.p. injection and returned to their home cage. After 4 hours of treatment, liver, spleen, blood (EDTA treated) and brain were perfused and collected. Liver was collected and analyzed on a DNA microarray chip as per manufacturer's directions and instruction from UIUC Keck Center. Spleen, blood, brain and extra liver samples were processed in RNAlater® and stored in a dedicated −20° C. freezer for future analysis.

Analysis:

For analysis the diets are referred to:
1. LF (D12450B: Control diet)
2. LFc+n (D11083104: Control diet+nucleotides+carotenoids)
3. 90% LF (D11083101: Calorie restriction)
4. 90%+n (D11083102: Calorie restriction+nucleotides)
5. 90%+c (D11083103: Calorie restriction+carotenoids)
6. 90%+c+n (D11083104: Calorie restriction+nucleotides+carotenoids)

Illumina's Mouse WG-6 v2 array (available from Illumina, San Diego, Calif. 92122 USA) has 45,281 unique probes; more than one probe can interrogate a single gene so there are not 45,281 unique genes on the array. Each probe was measured by ~45 beads on the array, and Illumina's Genome Studio (V2011.1, Gene Expression Module V1.9.0) was used to output the average value of all beads for each probe, without background correction or normalization. Additionally, the "Detection values" were output, which is the result of a t-test comparing the individual bead values for each probe to all the negative control beads on the array to see whether the probe's expression value was above background or not.

Inputs for the raw probe values and Detection P values in the R statistical package (v2.14.1) were done using the limma (linear model for microarray data) package. A pre-processing method called "neqc" was used on the raw probe values, which does a model-based background correction, a quantile between-array normalization and then log 2-transforms the resulting values. To be kept for further analysis, a probe had to be called "present" in at least 2 out of 4 replicates in any of the 12 treatment×diet combinations. 21,457 probes out of 45,281 passed this filter and were tested for differential expression using a statistical model with an empirical Bayes correction to help improve power to detect differences; the model also adjusted for the correlation between arrays on the same slide (the WG-6 format has 6 arrays per slide). The model first estimated the expression value for each of the 12 treatment×diet combinations then specific comparisons were pulled as contrasts from the model. There were many possible comparisons between the 12 treatment×diet groups; therefore, they were organized into 7 different sets:

1. LPSvPBS—the pairwise comparisons of LPS vs. PBS treatment within each diet; 6 comparisons total
2. PBSdiets—the pairwise comparisons of the different diets within PBS treatment
3. LPSdiets—the pairwise comparisons of the different diets within LPS treatment
4. PBS_2×2_90CandN—the 2×2 factorial comparison of adding C and/or N to the 90% LF within the PBS treatment. Comparisons include both main effects and the interaction term.
5. LPS_2×2_90CandN—the 2×2 factorial comparison of adding C and/or N to the 90% LF within the LPS treatment. Comparisons include both main effects and the interaction term.
6. PBS_2×2_CalAdd—the 2×2 factorial comparison of calorie level (90% vs. LF) and both C+N (yes vs. no) within the PBS treatment. Comparisons include both main effects and the interaction term.
7. LPS_2×2_CalAdd—the 2×2 factorial comparison of calorie level (90% vs. LF) and both C+N (yes vs. no) within the LPS treatment. Comparisons include both main effects and the interaction term.

PBS and LPS all pairwise (#2&3 above) datasets were further analyzed to determine genes of interest that were affected by the dietary treatments. Pairwise comparisons 3v2, 4v2, 5v2 and 6v2 were chosen to see if there were any relative differences in fold change between 4v2, 5v2, and 6v2 as compared to 3v2.

1. 3v2, 4v2, 5v2, and 6v2 comparison were extracted
2. Each list was sorted by the FDR p-value
3. Genes with a FDR p-value≥0.05 in 3v2 were identified
4. Genes with a FDR p-value≥0.05 in 4v2, 5v2, and 6v2 were identified
5. The genes in each individual pairwise comparison from step 4 were matched to those in step 3.
   a. Matching was done based on the probe ID number with the Countif function in Excel
6. Genes with a relative difference in fold change (more positive or more negative) were identified This resulted in 25 genes identified for 4v2 as compared to 3v2; 37 genes for 5v2 as compared to 3v2; and 23 genes for 6v2 as compared to 3v2 (FIG. 1) that had relative differences in fold change. These genes were hand sorted for relevance to the hypothesis. Search methods included use of GeneID number in PubMed searches as well as literature searches. This search identified three gene candidates that had a relative difference in fold change that would suggest a benefit of carotenoids and/or nucleotides to a reduced calorie diet.

Figure 2:
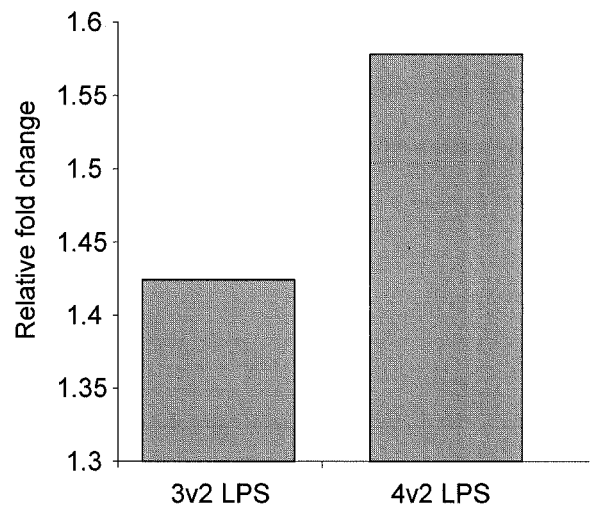
FIG. 2 depicts the relative increase in Prkab1/AMPKβ with the addition of nucleotides.
Figure 3:
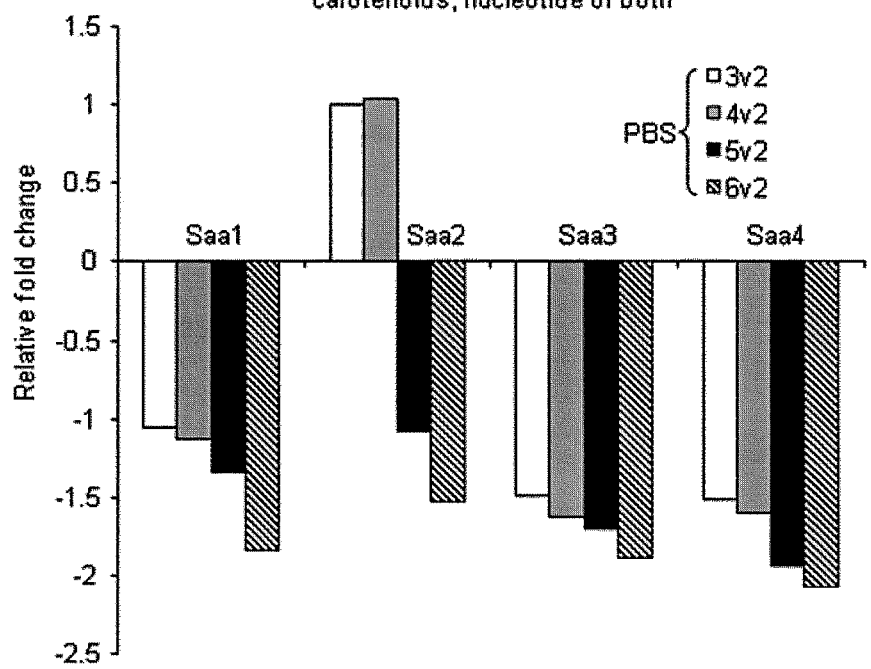
FIG. 3 depicts the relative decrease in Saa 1-4 with the addition of carotenoids, nucleotide, or both.
Figure 4:
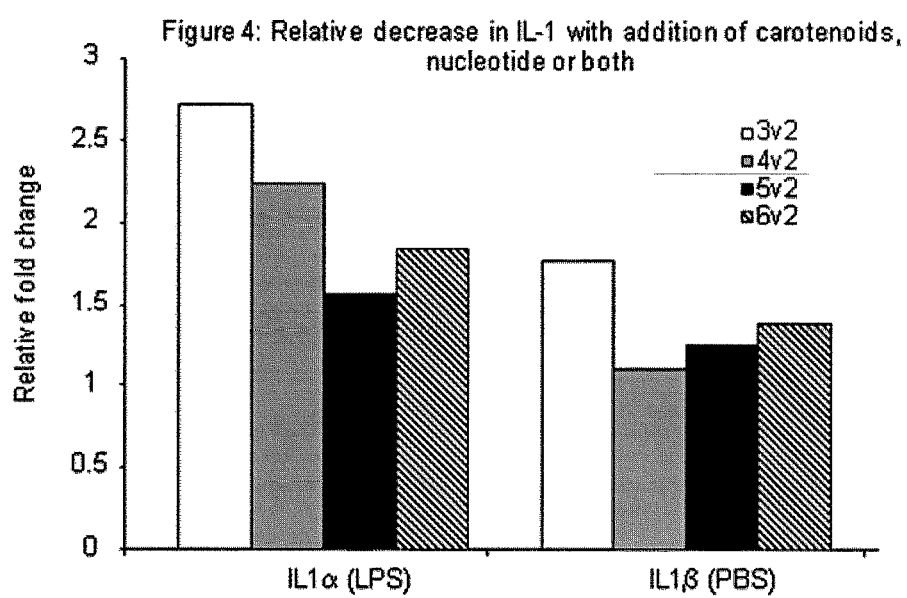
FIG. 4 depicts the relative decrease in IL-1 with addition of carotenoids, nucleotide, or both.

The genes identified are Prkab1/AMPKβ, serum amyloid A (Saa) and interleukin-1α/β (IL-1α/β). FIGS. 2-4 demonstrate the amount of absolute change in the fold-change of the diets of interest as compared to the reference diet. AMPK functions as a regulatory enzyme that 'turns on' ATP consuming catabolic pathways. Hepatic AMPK has been shown to regulate insulin and glucose metabolism. Obese humans have been shown to have decreased adipose tissue expression of AMPK that is related to obesity associated inflammation. Whole body knock-out (KO) of AMPK in mice leads to a reduced appetite and obesity prevention. This reduction in obesity is due to the decreased hypothalamic expression of AMPK leading to decreased food consumption (1). However, tissue specific (macrophages) increases in AMPK are related to a reduction in inflammation and insulin resistance in mice fed a high-fat diet (HFD) (2). FIG. 2 demonstrates that there is a relative increase in Prkab1/AMPKβ expression in LPS treated mice fed a reduced calorie diet as compared to those fed a reduced calorie diet with the addition of nucleotides (1.42 vs 1.58 fold change from control diet with carotenoids and nucleotides). Therefore, it is our hypothesis that the tissue specific (liver) increase in seen with addition of nucleotides to a reduced calorie diet may provide a benefit similar to that in Galic et al (2).

Serum amyloid A (SAA) is an acute phase protein that has been reported to be increased in the plasma of obese and insulin resistant humans (3). A recent meta-analysis and systematic review demonstrated a strong association between BMI and SAA levels in 11 cross-sectional studies (4). Chronic elevation of SAA has been associated with increased risk for atherosclerosis and is found in atherosclerotic lesions (5) where it has been shown to promote endothelial dysfunction (6). Scheja et al demonstrated that increased within a week of HFD feeding in mice and that ex-vivo treatment of adipocytes with SAA lead to an attenuation of insulin signaling and glucose transport (3). Serum amyloid A has been shown to decrease significantly after weight loss in obese subjects and the improvement in insulin sensitivity in these patients after weight loss was correlated with the decrease in SAA (7). FIG. 3 demonstrates that the addition of carotenoids, nucleotides and/or both to a reduced calorie diet results in a relative decrease in expression of Saa1-4. Therefore, it is our hypothesis that reduction in SAA expression in the liver (FIG. 3) may provide protective benefits to developing obesity, insulin resistance and/or atherosclerosis.

Interleukin 1α/β (IL-1) is a proinflammatory cytokine that has been shown to be increased in HFD and genetic models of obesity. Increased IL-1 is related to the chronic-low grade inflammation seen in obesity that is thought to be a key link between obesity and many of its co-morbidities, such as insulin resistance and atherosclerosis. Diabetic mice have an augmented IL-1β mediated immune response due to a loss of IL-1β counterregulation (8). Polymorphisms in IL-1α have been associated with obesity in healthy obese subjects (9, 10). IL-1α has been shown to be increased in obese mice (HFD model) as well as acute increases in triglyceride levels (10). There is a relative decrease in expression of IL-1α in LPS treated mice fed a reduced calorie diet with the addition of carotenoids, nucleotides and/or both as compared to a control diet with carotenoids and nucleotide. Additionally, this same pattern of reduce expression can be seen with IL-1β in PBS treated mice (FIG. 4). Reduction in IL-1α/β is anti-inflammatory and it is our hypothesis that this reduction as seen with addition of carotenoids and/or nucleotides to a reduced calorie diet, will provide an additional anti-inflammatory benefit and protection from obesity and its immune mediated co-morbidities.

REFERENCES

1. Dzamko N, van Denderen B J, Hevener A L, Jorgensen S B, Honeyman J, Galic S, et al. AMPK beta1 deletion reduces appetite, preventing obesity and hepatic insulin resistance. J Biol Chem. 2010 Jan. 1; 285(1):115-22.
2. Galic S, Fullerton M D, Schertzer J D, Sikkema S, Marcinko K, Walkley C R, et al. Hematopoietic AMPK beta1 reduces mouse adipose tissue macrophage inflammation and insulin resistance in obesity. J Clin Invest. 2011 December; 121(12):4903-15.
3. Scheja L, Heese B, Zitzer H, Michael M D, Siesky A M, Pospisil H, et al. Acute-phase serum amyloid A as a marker of insulin resistance in mice. Exp Diabetes Res. 2008; 2008:230837.
4. Zhao Y, He X, Shi X, Huang C, Liu J, Zhou S, et al. Association between serum amyloid A and obesity: a meta-analysis and systematic review. Inflamm Res. 2010 May; 59(5):323-34.
5. King V L, Thompson J, Tannock L R. Serum amyloid A in atherosclerosis. Curr Opin Lipidol. 2011 August; 22(4): 302-7.
6. Witting P K, Song C, Hsu K, Hua S, Parry S N, Aran R, et al. The acute-phase protein serum amyloid A induces endothelial dysfunction that is inhibited by high-density lipoprotein. Free Radic Biol Med. 2011 Oct. 1; 51(7): 1390-8.
7. Yang R Z, Lee M J, Hu H, Pollin T I, Ryan A S, Nicklas B J, et al. Acute-phase serum amyloid A: an inflammatory adipokine and potential link between obesity and its metabolic complications. PLoS Med. 2006 June; 3(6): e287.
8. O'Connor J C, Satpathy A, Hartman M E, Horvath E M, Kelley K W, Dantzer R, et al. IL-1 beta-mediated innate immunity is amplified in the db/db mouse model of type 2 diabetes. J. Immunol. 2005 Apr. 15; 174(8):4991-7.
9. Song J S, Jeong H J, Kim S J, Son M S, Na H J, Song Y S, et al. Interleukin-1alpha polymorphism −889C/T related to obesity in Korean Taeumin women. Am J Chin Med. 2008; 36(1):71-80.
10. Urn J Y, Rim H K, Kim S J, Kim H L, Hong S H. Functional polymorphism of IL-1 alpha and its potential role in obesity in humans and mice. PLoS One. 2011; 6(12):e29524.

TABLE 3

Rodent Diet with 10 kcal % Fat and Same with 10% Calorie Restriction, with Nucleotides and/or Carotenoids

| | D12450B Control | | D11083101 10% Restriction | | D11083102 10% CR + Nucleo | | D11083103 10% CR + Carot | | D11083104 10% CR + Nucleo, Carot | |
|---|---|---|---|---|---|---|---|---|---|---|
| | gm | kcal | gm | kcal | gm | kcal | gm | kcal | gm | kcal |
| % | | | | | | | | | | |
| Protein | 19.2 | 20 | 17.4 | 19 | 17.4 | 19 | 17.4 | 19 | 17.4 | 19 |
| Carbohydrate | 67.3 | 70 | 69.5 | 74 | 69.5 | 74 | 69.5 | 74 | 69.5 | 74 |
| Fat | 4.3 | 10 | 3.1 | 7 | 3.1 | 7 | 3.1 | 7 | 3.1 | 7 |
| Total | | 100 | | 100 | | 100 | | 100 | | 100 |
| kcal/gm | 3.85 | | 3.76 | | 3.75 | | 3.75 | | 3.75 | |
| Ingredient | | | | | | | | | | |
| Casein, 80 Mesh | 200 | 800 | 166.8 | 667 | 166.8 | 667 | 166.8 | 667 | 166.8 | 667 |
| L-Cystine | 3 | 12 | 2.5 | 10 | 2.5 | 10 | 2.5 | 10 | 2.5 | 10 |
| Corn Starch | 315 | 1260 | 298 | 1192 | 298 | 1192 | 298 | 1192 | 298 | 1192 |
| Maltodextrin 10 | 35 | 140 | 35 | 140 | 35 | 140 | 35 | 140 | 35 | 140 |
| Sucrose | 350 | 1400 | 333 | 1332 | 333 | 1332 | 333 | 1332 | 333 | 1332 |
| Cellulose, BW200 | 50 | 0 | 50 | 0 | 50 | 0 | 50 | 0 | 50 | 0 |
| Soybean Oil | 25 | 225 | 16.7 | 150 | 16.7 | 150 | 16.7 | 150 | 16.7 | 150 |
| Lard | 20 | 180 | 13.3 | 120 | 13.3 | 120 | 13.3 | 120 | 13.3 | 120 |

TABLE 3-continued

Rodent Diet with 10 kcal % Fat and Same with 10% Calorie Restriction, with Nucleotides and/or Carotenoids

| | D12450B Control | | D11083101 10% Restriction | | D11083102 10% CR + Nucleo | | D11083103 10% CR + Carot | | D11083104 10% CR + Nucleo, Carot | |
|---|---|---|---|---|---|---|---|---|---|---|
| | gm | kcal | gm | kcal | gm | kcal | gm | kcal | gm | kcal |
| Mineral Mix S10026 | 10 | 0 | 10 | 0 | 10 | 0 | 10 | 0 | 10 | 0 |
| DiCalcium Phosphate | 13 | 0 | 13 | 0 | 13 | 0 | 13 | 0 | 13 | 0 |
| Calcium Carbonate | 5.5 | 0 | 5.5 | 0 | 5.5 | 0 | 5.5 | 0 | 5.5 | 0 |
| Potassium Citrate, 1 H2O | 16.5 | 0 | 16.5 | 0 | 16.5 | 0 | 16.5 | 0 | 16.5 | 0 |
| Vitamin Mix V10001 | 10 | 40 | 10 | 40 | 10 | 40 | 10 | 40 | 10 | 40 |
| Choline Bitartrate | 2 | 0 | 2 | 0 | 2 | 0 | 2 | 0 | 2 | 0 |
| Nucleotides | 0 | 0 | 0 | 0 | 0.5 | 0 | 0 | 0 | 0.5 | 0 |
| Carotenoids | 0 | 0 | 0 | 0 | 0 | 0 | 0.03 | 0 | 0.03 | 0 |
| FD&C Yellow Dye #5 | 0.05 | 0 | 0.025 | 0 | 0 | 0 | 0 | 0 | 0 | 0 |
| FD&C Red Dye #40 | 0 | 0 | 0.025 | 0 | 0 | 0 | 0.05 | 0 | 0.025 | 0 |
| FD&C Blue Dye #1 | 0 | 0 | 0 | 0 | 0.5 | 0 | 0 | 0 | 0.025 | 0 |
| Total | 1055.05 | 4057 | 972.35 | 3651 | 973.3 | 3651 | 972.38 | 3651 | 972.88 | 3651 |

D11083101: To feed 10% fewer calories, feed 0.92 gm for every gram of D12450B

What is claimed is:

1. A method of reducing an infant's risk of developing obesity later in life, the method comprising administering to an infant an infant formula in the first year of life, wherein the infant formula has an energy content of less than 650 Kcal/L and comprises a nucleotide and a carotenoid as active ingredients to reduce the infant's risk of developing obesity later in life, wherein the infant formula comprises from 42 mg/L to 102 mg/L of nucleotide.

2. The method of claim 1, wherein the infant formula further comprises less than 14.0 grams of protein per liter of formula.

3. The method according to claim 1, wherein the nucleotide is selected from the group consisting of cytidine 5' monophosphate, disodium guanosine 5' monophosphate, disodium uridine 5' monophosphate, adenosine 5' monophosphate, and combinations thereof.

4. The method according to claim 1, wherein the infant formula comprises from 0.001 mg/L to 5 mg/L of carotenoid.

5. The method according to claim 1, wherein the carotenoid is selected from the group consisting of lutein, lycopene, zeaxanthin, beta-carotene, and combinations thereof.

6. The method according to claim 1, wherein the carotenoid is lutein.

7. The method according to claim 2, wherein the infant formula comprises from 5.0 grams to 10.0 grams of protein per liter of formula.

8. The method according to claim 4, wherein the infant formula comprises from 0.01 mg/L to 1 mg/L of carotenoid.

9. A method of reducing an infant's risk of developing obesity later in life, the method comprising administering to an infant an infant formula in the first year of life, wherein the infant formula has an energy content of from 200 Kcal/L to 600 Kcal/L and comprises a carotenoid as an active ingredient to reduce the infant's risk of developing obesity later in life.

10. The method of claim 9, wherein the infant formula further comprises less than 14.0 grams of protein per liter of formula.

11. The method according to claim 9, wherein the infant formula further comprises from 10 mg/L to 200 mg/L of a nucleotide.

12. The method according to claim 11, wherein the nucleotide is selected from the group consisting of cytidine 5' monophosphate, disodium guanosine 5' monophosphate, disodium uridine 5' monophosphate, adenosine 5' monophosphate, and combinations thereof.

13. The method according to claim 9, wherein the infant formula comprises from 0.001 mg/L to 5 mg/L of carotenoid.

14. The method according to claim 9, wherein the carotenoid is selected from the group consisting of lutein, lycopene, zeaxanthin, beta-carotene, and combinations thereof.

15. The method according to claim 9, wherein the carotenoid is lutein.

16. A method of reducing an infant's risk of developing obesity later in life, the method comprising administering to an infant an infant formula in the first year of life, wherein the infant formula has an energy content of less than 650 Kcal/L and comprises from 42 mg/L to 200 mg/L of a nucleotide as an active ingredient to reduce the infant's risk of developing obesity later in life.

* * * * *